(12) United States Patent
Pajotin

(10) Patent No.: US 6,723,133 B1
(45) Date of Patent: Apr. 20, 2004

(54) PERFORMED CURVED PROSTHESIS HAVING A REDUCED INCIDENCE OF DEVELOPING WRINKLES OR FOLDS

(75) Inventor: Philippe Pajotin, Cholet (FR)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/786,931

(22) PCT Filed: Sep. 10, 1999

(86) PCT No.: PCT/US99/20933

§ 371 (c)(1),
(2), (4) Date: Jul. 5, 2001

(87) PCT Pub. No.: WO00/15142

PCT Pub. Date: Mar. 23, 2000

(30) Foreign Application Priority Data

Sep. 11, 1998 (FR) .......................................... 98 11331

(51) Int. Cl.$^7$ ................................................. A61F 2/02
(52) U.S. Cl. ..................................... 623/23.72; 606/151
(58) Field of Search ............................. 623/6.23, 6.24, 623/14.13, 23.72, 11.11, 8, 20.22, 23.64; 600/37; 606/151

(56) References Cited

U.S. PATENT DOCUMENTS

| 2,671,444 A | 3/1954 | Pease |
|---|---|---|
| 3,559,214 A | 2/1971 | Pangman |
| 3,805,301 A | 4/1974 | Liebig |
| 3,875,928 A | 4/1975 | Angelchik |
| 3,988,411 A | 10/1976 | Capozza |
| 4,345,414 A | 8/1982 | Bornat et al. |
| 4,403,604 A | 9/1983 | Wilkinson et al. |
| 4,441,215 A | 4/1984 | Kaster |
| 4,545,082 A | 10/1985 | Hood |
| 4,555,378 A | 11/1985 | Martin et al. |
| 4,573,999 A | 3/1986 | Netto |

(List continued on next page.)

FOREIGN PATENT DOCUMENTS

| AU | 593 267 B | 1/1988 |
|---|---|---|
| DE | 40 13 447 C1 | 2/1992 |

(List continued on next page.)

*Primary Examiner*—Nicholas D. Lucchesi
*Assistant Examiner*—Fenn C Mathew
(74) *Attorney, Agent, or Firm*—Wolf, Greenfield & Sacks, P.C.

(57) ABSTRACT

A prosthesis is provide for repairing a defect in a muscle or tissue wall. The prosthesis has a preformed shape that conforms to the wall to facilitate placement and minimize shifting of the prosthesis when positioned on the wall. The prosthesis may include a body formed of a sheet of surgical mesh fabric having a flexible body surrounded by a peripheral edge that may be welded or fused so that the body is capable of resuming the preformed shape after being temporarily deformed to allow for implantation. In one embodiment, the body includes a first portion (1) configured with a substantially spherical shape and a second portion (6) connected to the first portion at an outer edge (2) thereof, wherein the first portion has a first radius of curvature and the second portion has a second radius of curvature that is substantially equal to the first radius of curvature along the outer edge (2). This configuration reduces the incidence of puckering between the first and second portions which otherwise could reduce the overall size of the prosthesis resulting less than a desirable amount of wall coverage.

19 Claims, 1 Drawing Sheet

U.S. PATENT DOCUMENTS

| | | | |
|---|---|---|---|
| 4,693,720 A | | 9/1987 | Scharnberg et al. |
| 4,728,328 A | | 3/1988 | Hughes et al. |
| 4,841,948 A | | 6/1989 | Bauer et al. |
| 5,061,277 A | | 10/1991 | Carpentier et al. |
| 5,112,352 A | * | 5/1992 | Novack ............... 623/8 |
| 5,116,370 A | * | 5/1992 | Foglietti ............. 623/8 |
| 5,146,933 A | | 9/1992 | Boyd |
| 5,147,398 A | * | 9/1992 | Lynn et al. .......... 623/8 |
| 5,236,454 A | | 8/1993 | Miller |
| 5,258,000 A | | 11/1993 | Gianturco |
| 5,292,328 A | | 3/1994 | Hain et al. |
| 5,306,296 A | | 4/1994 | Wright et al. |
| 5,356,429 A | * | 10/1994 | Seare ................. 623/8 |
| 5,356,432 A | * | 10/1994 | Rutkow et al. ....... 600/37 |
| 5,366,460 A | | 11/1994 | Eberbach |
| 5,383,477 A | | 1/1995 | DeMatteis |
| 5,383,925 A | | 1/1995 | Schmitt |
| 5,443,508 A | * | 8/1995 | Giampapa .......... 424/424 |
| 5,456,720 A | | 10/1995 | Schultz et al. |
| 5,466,258 A | * | 11/1995 | Rubin ............... 623/5.11 |
| 5,584,884 A | * | 12/1996 | Pignataro ............ 623/8 |
| 5,593,441 A | | 1/1997 | Lichtenstein et al. |
| 5,674,279 A | | 10/1997 | Wright et al. |
| 5,676,146 A | | 10/1997 | Scarborough |
| 5,695,525 A | | 12/1997 | Mulhauser et al. |
| 5,702,459 A | * | 12/1997 | Hummer et al. ....... 623/20.18 |
| 5,716,404 A | * | 2/1998 | Vacanti et al. ....... 623/8 |
| 5,716,408 A | | 2/1998 | Eldridge et al. |
| 5,725,577 A | | 3/1998 | Saxon |
| 5,743,917 A | | 4/1998 | Saxon |
| 5,766,246 A | | 6/1998 | Mulhauser et al. |
| 5,769,864 A | | 6/1998 | Kugel |
| 5,796,462 A | * | 8/1998 | Roffman et al. ....... 351/160 H |
| 5,865,728 A | | 2/1999 | Moll et al. |
| 5,895,424 A | | 4/1999 | Steele, Sr. et al. |
| 5,954,767 A | * | 9/1999 | Pajotin et al. ........ 606/215 |
| 6,004,333 A | | 12/1999 | Sheffield et al. |
| 6,024,763 A | | 2/2000 | Lenker et al. |
| 6,042,592 A | | 3/2000 | Schmitt |
| 6,066,776 A | | 5/2000 | Goodwin et al. |
| 6,066,777 A | | 5/2000 | Benchetrit |
| 6,074,419 A | | 6/2000 | Healy et al. |
| 6,090,116 A | | 7/2000 | D'Aversa et al. |
| 6,096,044 A | | 8/2000 | Boyd et al. |
| 6,113,623 A | | 9/2000 | Sgro |
| 6,120,434 A | | 9/2000 | Kimura et al. |
| 6,120,539 A | | 9/2000 | Eldridge et al. |
| 6,162,962 A | | 12/2000 | Hinsch et al. |
| 6,171,318 B1 | | 1/2001 | Kugel et al. |
| 6,174,320 B1 | | 1/2001 | Kugel et al. |
| 6,176,863 B1 | | 1/2001 | Kugel et al. |
| 6,214,020 B1 | | 4/2001 | Mulhauser et al. |
| 6,224,616 B1 | | 5/2001 | Kugel |
| 6,241,768 B1 | | 6/2001 | Agarwal et al. |
| 6,258,124 B1 | | 7/2001 | Darois et al. |
| 6,264,702 B1 | | 7/2001 | Ory et al. |
| 6,267,772 B1 | | 7/2001 | Mulhauser et al. |
| 6,270,530 B1 | | 8/2001 | Eldridge et al. |
| 6,280,453 B1 | | 8/2001 | Kugel et al. |
| 6,287,293 B1 | | 9/2001 | Jones et al. |
| 6,287,316 B1 | | 9/2001 | Agarwal et al. |
| 6,290,708 B1 | | 9/2001 | Kugel et al. |
| 6,306,154 B1 | | 10/2001 | Hudson et al. |
| 6,312,442 B1 | | 11/2001 | Kieturakis et al. |
| 6,312,456 B1 | | 11/2001 | Kranz et al. |
| 6,319,264 B1 | | 11/2001 | Törmäläet al. |
| 6,368,541 B1 | | 4/2002 | Pajotin et al. |
| 6,451,139 B1 | * | 9/2002 | Weber-Unger et al. ....... 156/61 |
| 2001/0027347 A1 | | 10/2001 | Rousseau |
| 2001/0034528 A1 | | 10/2001 | Foerster et al. |
| 2001/0049538 A1 | | 12/2001 | Trabucco |
| 2001/0049539 A1 | | 12/2001 | Rehil |
| 2001/0053919 A1 | | 12/2001 | Kieturakis et al |

FOREIGN PATENT DOCUMENTS

| | | |
|---|---|---|
| EP | 0 573 273 A2 | 12/1993 |
| EP | 0 592 244 A2 | 4/1994 |
| EP | 0 614 650 A2 | 9/1994 |
| EP | 0 836 838 A1 | 4/1998 |
| EP | 1 145 693 A2 | 10/2001 |
| FR | 2 682 284 A1 | 4/1993 |
| GB | 2 226 762 A | 7/1990 |
| JP | 7000430 | 1/1995 |
| WO | WO 92/13500 A1 | 8/1992 |
| WO | WO 95/07666 A1 | 3/1995 |
| WO | WO 96/03091 A1 | 2/1996 |
| WO | WO 96/41588 A1 | 12/1996 |
| WO | WO 99/03422 A1 | 1/1999 |
| WO | WO 00/15141 A1 | 3/2000 |
| WO | WO 00/42943 A1 | 7/2000 |
| WO | WO 01/15625 A1 | 3/2001 |
| WO | WO 01/80773 A1 | 11/2001 |

* cited by examiner

PERFORMED CURVED PROSTHESIS HAVING A REDUCED INCIDENCE OF DEVELOPING WRINKLES OR FOLDS

RELATED APPLICATIONS

This application is a national stage filing under 35 U.S.C. §371 of PCT International application No. PCT/US99/20933, filed Sep. 10, 1999, which was published in English under PCT Article 21(2).

BACKGROUND OF THE INVENTION

1. Field of the Invention

The present invention relates to an implantable prosthesis, and more particularly to a prosthesis for repairing a hernia.

2. Description of the Related Art

A defect in a muscle or tissue wall, such as a hernia, is commonly repaired with an implantable prosthesis that is configured to cover and/or fill the defect. In many instances, a flat sheet of an implantable, non-resorbable, flexible mesh material, such as BARD MESH, has been employed for the parietal repair of hernias and eventrations of the abdominal wall. However, a surgeon may experience some difficulty positioning the mesh between the parietal peritoneum and the abdominopelvic wall. The mesh may also fold or wrinkle and be difficult to maintain in position.

Applicant previously developed an implantable prosthesis for repairing a defect in a muscle or tissue wall to alleviate some of these concerns. The prosthesis, which is disclosed in WO 95/07666 and is assigned to C. R. Bard, the assignee of the present application, is made of an implantable, nonabsorbable and flexible material that is formed to independently assume a curved shape adapted to conform to the anatomical shape of the wall. The prosthesis includes a body comprised of a first portion having a substantially spherical shape and a second portion connected to an outer edge of the first portion.

This prosthesis has proven useful and has become established in the practice of muscle or tissue wall repair in the inguinofemoral region. The prosthesis is not subject to stresses when deformed and, therefore, has no tendency to shift upon implantation.

It has nevertheless been observed that the prosthesis at times may wrinkle or fold between the first and second portions, thereby reducing the overall size of the prosthesis which may result in a prosthesis that does not adequately cover the region being repaired.

It is an object of the present invention to provide an improved prosthesis for repairing a defect in a muscle or tissue wall.

SUMMARY OF THE INVENTION

The present invention is an implantable prosthesis for repairing a defect in a muscle or tissue wall. The prosthesis includes a body of prosthetic material having a preformed three-dimensional contoured shape that independently assumes a curved shape adapted to conform to the wall. The body includes a first portion that is configured with a substantially spherical shape and a second portion that is connected to the first portion at an outer edge thereof. The body is configured to substantially reduce the incidence of wrinkles or folds between the first and second portions so that the first and second portions do not partially cover each other upon or after implantation, thereby ensuring that the overall size of the prosthesis is sufficient to adequately cover the desired portion of the wall.

According to one embodiment of the invention, the first portion has a first radius of curvature and the second portion has a second radius of curvature that is substantially equal to the first radius of curvature along the outer edge.

According to another aspect of the invention, the first portion includes a first lower edge and the second portion includes a second lower edge, and the body further includes a third portion connected to the first lower edge and a fourth portion connected to the second lower edge. Each of the third and fourth portions is configured with a substantially spherical shape to enhance conformance to a particular anatomical shape.

According to a further aspect of the invention, the prosthesis has a total surface area greater than approximately 40,000 mm$^2$.

According to still another aspect of the invention, the prosthesis is configured with a ratio of the surface area of the second portion to the total surface area of the prosthesis from approximately 0.25 to approximately 0.40.

BRIEF DESCRIPTION OF THE DRAWINGS

The foregoing and other objects and advantages of the invention will be appreciated ore fully from the following drawings, given solely by way of example, in which.

DETAILED DESCRIPTION

Figure 3:
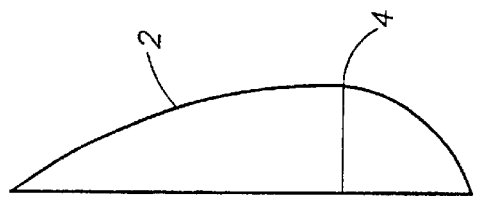
FIG. 3 is a cross-sectional view of the prosthesis taken along section line III—III in FIG. 1.
Figure 2:
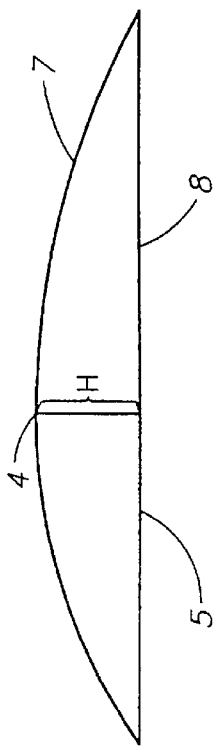
FIG. 2 is a cross-sectional view of the prosthesis taken along section line II—II in FIG. 1.
Figure 1:
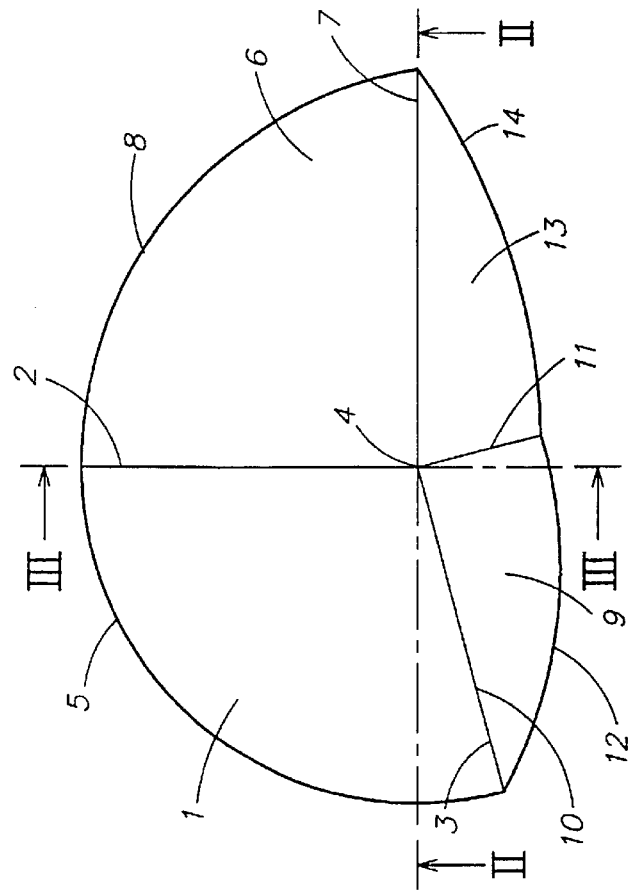
FIG. 1 is a plan view of a prosthesis according to one illustrative embodiment of the invention.

FIGS. 1–3 illustrate one embodiment of a prosthesis for repairing a defect in a muscle or tissue wall, such as a hernia. The prosthesis includes a body of prosthetic material that is preformed with a three-dimensional configuration that conforms to the anatomical shape of the defective wall to facilitate placement and minimize shifting of the prosthesis when positioned on the wall. The body includes a plurality of shaped portions that are joined to each other to create a desired configuration.

In one illustrative embodiment, the body includes first, second, third and fourth portions 1, 6, 9, 13, respectively, that are connected to each other to form a unitary structure. Each of the portions includes a curved surface that provide the prosthesis with the preformed contoured shape.

The first portion 1 is formed with a substantially spherical shape and includes a first outer edge 2 and a first lower edge 3 joined to each other at an apex 4 of the prosthesis, which is the highest point thereof. The first portion 1 also includes a circular inner edge 5 that extends in the same plane as the outer and lower edges 2, 3.

The second portion 6, which lies adjacent the first portion 1, includes a second lower edge 7 and a circular second outer edge 8. The second portion 6 is connected to the first portion 1 along the first outer edge 2.

The third portion 9 is disposed below the first portion 1 and includes an upper edge 10, a third outer edge 11 and a curved third lower edge 12. As shown, the upper edge 10 merges with the first lower edge 3 of the first portion.

The fourth portion 13 is positioned below the second portion 6 and adjacent the third portion 9. The fourth portion 13 is defined by and is connected to the second lower edge 7 of the second portion 6 and the third outer edge 11 of the third portion 9. The fourth portion also includes a curved fourth lower edge 14.

As illustrated in FIG. 1, the inner edge 5, the second outer edge 8 and the third and fourth lower edges 12, 14 form a generally D-shaped peripheral edge of the prosthesis. The peripheral edge may be welded or fused so that the body can regain its contoured shape after being deformed during implantation.

Each of the third and fourth portions 9, 13 may also have substantially spherical shapes to enhance conformance to a particular anatomical shape. In one illustrative embodiment, the radius of curvature of the third and fourth portions is less than the radius of curvature of the first portion to form surfaces in the third and fourth portions that have a steeper incline relative to the first portion.

The third and fourth portions are shaped to form a depression in the surface of the body that is configured to receive the iliac vessels when the prosthesis is employed for inguinal hernia repair. The depression extends inwardly from the peripheral edge between the third and fourth lower edges 12, 14 toward the apex 4.

The prosthesis may be formed from an implantable, biologically compatible material that is nonabsorbable and flexible. In one embodiment, the prosthesis is formed of a knitted fabric of implantable polypropylene filament, such as BARD MESH, that includes a plurality of interstices (not shown) for promoting tissue ingrowth to the prosthesis. It is to be understood, however, that the prosthesis may be formed of any suitable material.

The prosthesis may be configured to have any shape and size suitable for a particular application. In one embodiment, the height H of the prosthesis from a plane defined by the peripheral edge and the apex 4 is approximately 21 mm. The first portion 1 has a substantially spherical shape with a radius of curvature of approximately 120 mm, particularly along the first outer edge 2. The second portion 6 has substantially the same radius of curvature of approximately 120 mm adjacent the first outer edge 2. The third and fourth portions 9, 13 each has a substantially spherical shape with a radius of curvature of approximately 35 mm. The total surface area of the prosthesis is approximately 44,780 mm$^2$, with the second portion 10 having a surface area of approximately 12,735 mm$^2$.

The disclosed configuration is particularly suited for repairing an inguinal hernia. It is to be appreciated, however, that this configuration is exemplary and that the prosthesis may be configured to have other shapes and sizes suitable for a particular application.

The preformed curved shape of the prosthesis may be obtained using a thermoforming procedure. In one illustrative embodiment the thermoforming procedure includes placing a sheet of mesh fabric in a mold having the desired shape for the prosthesis, heating the fabric in the mold at an approximate temperature of 100° C. to 200° C. for a period of approximately 5 to 60 minutes, and subsequently cooling the fabric in the mold with an air flow having an approximate temperature of 15° C. to 30° C. for a period of approximately 5 to 60 minutes.

The edges of the prosthesis may be welded by fusing the meshes and the material using an ultrasonic welding procedure. During this procedure, the prosthesis is maintained between an element generating vibrations and an anvil that is configured to the particular dimensions of the prosthesis. In one embodiment, the edges are welded at a pressure of approximately 150 kPa to 800 kPa and an energy of approximately 100 to 5000 joules for a period of approximately 50 to 5000 milliseconds.

Once the sheet of mesh fabric has been shaped and the edges of the shaped prosthesis have been welded, any excess fabric extending beyond the welded edges is separated from the body of the prosthesis using a manual cutting procedure to form the completed prosthesis.

After inspection, the prosthesis may be packed in an internal packing (shell and insert) that has been designed specifically according to the three-dimensional characteristics of the prosthesis so as to comply with and protect the preformed curved shape of the prosthesis. The internal packing may be subsequently placed and packaged in a external packing for additional protection. The entire assembly may then be sterilized using any suitable method, such as with ethylene oxide, to provide a sterile prosthesis that is ready for implantation.

It should be understood that the foregoing description of the invention is intended merely to be illustrative thereof and that other embodiments, modifications, and equivalents of the invention are within the scope of the invention recited in the claims appended hereto.

What is claimed is:

1. An implantable prosthesis for repairing a defect in a muscle or tissue wall, the prothesis comprising:

a body of prosthetic material having a preformed three-dimensional contoured shape that independently assumes a curved shape adapted to conform to the wall, the body including a first portion configured with a substantially spherical-shaped surface and a second portion connected to the first portion at an outer edge thereof, wherein the second portion has a shape that is distinct from the first portion, the first portion having a first radius of curvature and the second portion having a second radius of curvature that is substantially equal to the first radius of curvature along the outer edge in a direction perpendicular to the outer edge.

2. The prosthesis according to claim 1, wherein the second portion terminates in an end opposite the outer edge and has a curved shape extending from the outer edge to the end in a direction perpendicular to the outer edge.

3. The prosthesis according to claim 2, wherein the end of the second portion includes a pointed tip.

4. The prosthesis according to claim 2, wherein the second radius of curvature differs from the first radius of curvature along a segment of the second portion between the outer edge and the end thereof.

5. The prosthesis according to claim 1, wherein the first portion includes a first lower edge and the second portion includes a second lower edge, and wherein the body includes a third portion connected to the first lower edge and a fourth portion connected to the second lower edge, each of the third and fourth portions configured with a substantially spherical-shaped surface.

6. The prothesis according to claim 1, wherein the second portion has a surface area and the body has a total surface area, the prosthesis being configured with a ratio of the surface area of the second portion to the total surface area that ranges from approximately 0.25 to approximately 0.40.

7. The prosthesis according to claim 6, wherein the total surface area is greater than approximately 40,000 mm$^2$.

8. The prosthesis according to claim 5, wherein the body includes a permanent depression between the third portion and the fourth portion, the depression being constructed and arranged to be placed proximate the external iliac vessels when the prosthesis is positioned on the wall to repair an inguinal hernia.

9. The prosthesis according to claim 8, wherein the body includes an apex, the depression extending inwardly from a peripheral edge of the body toward the apex.

10. The prosthesis according to claim 5, wherein the third portion has a third radius of curvature and the fourth portion has a fourth radius of curvature that is substantially equal to the third radius of curvature.

11. The prosthesis according to claim 10, wherein the third radius of curvature is approximately 35 mm.

12. The prosthesis according to claim 5, each of the third and fourth portions includes a curved lower edge.

13. The prosthesis according to claim 1, wherein the body includes a peripheral edge that is generally D-shaped.

14. The prosthesis according to claim 1, wherein the first radius of curvature is approximately 120 mm.

15. The prosthesis according to claim 1, wherein the body of prosthetic material includes surgical mesh.

16. The prosthesis according to claim 1, wherein the body includes a peripheral edge that is configured to allow the body to regain the contoured shape after being deformed.

17. The prosthesis according to claim 1, wherein the body includes no more than four distinctly shaped portions.

18. The prosthesis according to claim 17, wherein the body consists essentially of the four distinctly-shaped portions.

19. The prosthesis according to claim 17, wherein the first portion includes a first lower edge and the second portion includes a second lower edge, and wherein the body includes a third portion connected to the first lower edge and a fourth portion connected to the second lower edge, each of the third and fourth portions configured with a shape that is distinct from each other and the first and second portions.

* * * * *

UNITED STATES PATENT AND TRADEMARK OFFICE
CERTIFICATE OF CORRECTION

PATENT NO. : 6,723,133 B1  
DATED : April 20, 2004  
INVENTOR(S) : Philippe Pajotin Page 1 of 1

It is certified that error appears in the above-identified patent and that said Letters Patent is hereby corrected as shown below:

Title page,
Item [54], Title, replace "PERFORMED CURVED PROSTHESIS HAVING A REDUCED INCIDENCE OF DEVELOPING WRINKLES OR FOLDS" with
-- PREFORMED CURVED PROSTHESIS HAVING A REDUCED INCIDENCE OF DEVELOPING WRINKLES OR FOLDS --.
Item [57], ABSTRACT,
Line 1, replace "provide" with -- provided --.
Line 10, insert -- in -- after "resulting".

Signed and Sealed this

Seventh Day of September, 2004

JON W. DUDAS
*Director of the United States Patent and Trademark Office*